United States Patent [19]

Bowman et al.

[11] Patent Number: 4,922,024

[45] Date of Patent: May 1, 1990

[54] AMINATION PROCESS EMPLOYING GROUP VIB METAL CATALYSTS

[75] Inventors: Robert G. Bowman; Marvin H. Tegen; George E. Hartwell, Midland, Mich.

[73] Assignee: The Dow Chemical Company, Midland, Mich.

[21] Appl. No.: 181,622

[22] Filed: Apr. 14, 1988

[51] Int. Cl.$^5$ .................. C07C 85/06; C07D 295/02; C07D 295/12

[52] U.S. Cl. .................... 564/480; 564/346; 564/355; 564/360; 564/367; 564/368; 564/372; 564/401; 564/402; 544/358; 544/402

[58] Field of Search ............ 564/480, 346, 355, 360, 564/367, 368, 372, 401, 402; 502/177, 204, 206; 544/358, 402

[56] References Cited

U.S. PATENT DOCUMENTS

| | | |
|---|---|---|
| 1,875,746 | 9/1932 | Martin et al. |
| 2,033,866 | 5/1936 | Schrauth ............................ 260/127 |
| 2,082,105 | 6/1937 | Herold et al. ...................... 260/127 |
| 2,285,419 | 6/1942 | Dickey et al. ..................... 260/584 |
| 2,394,516 | 2/1946 | Goshorn ............................. 260/583 |
| 2,591,493 | 4/1952 | Arnold et al. .................... 260/465.2 |
| 3,037,023 | 5/1962 | Moss et al. ........................ 260/268 |
| 3,231,616 | 1/1966 | Jones .................................. 260/581 |
| 3,272,865 | 9/1966 | Barker ................................ 260/581 |
| 3,285,920 | 11/1966 | Muhlbauer et al. ................ 260/268 |
| 3,383,417 | 5/1968 | Lichtenwalter .................... 260/584 |
| 3,475,344 | 6/1969 | Adam et al. ....................... 252/432 |
| 3,491,148 | 1/1970 | Winderl et al. .................... 260/563 |
| 3,510,518 | 5/1970 | Gaydasch .......................... 260/576 |
| 3,714,259 | 1/1973 | Lichtenwalter et al. .......... 260/583 R |
| 3,875,235 | 4/1975 | Noeske et al. .................... 260/585 B |
| 4,206,150 | 6/1980 | Slaugh et al. ..................... 260/583 R |
| 4,217,240 | 8/1980 | Bergna .............................. 252/313 S |
| 4,314,083 | 2/1982 | Ford et al. ......................... 564/479 |
| 4,325,843 | 4/1982 | Slaugh et al. ..................... 252/443 |
| 4,404,399 | 9/1983 | Kochar .............................. 564/402 |
| 4,495,369 | 1/1985 | Werner et al. .................... 564/480 |
| 4,647,701 | 3/1987 | Gibson .............................. 564/479 |
| 4,683,335 | 7/1987 | Knifton et al. ................... 564/480 |
| 4,740,490 | 4/1988 | Vanderspurt et al. ............ 502/177 |

FOREIGN PATENT DOCUMENTS 48-96475 12/1973 Japan.

OTHER PUBLICATIONS

Derwent 85-307986/49.
Derwent 70474 C/40.
Derwent 12224 V/07.

*Primary Examiner*—Richard L. Raymond
*Assistant Examiner*—Peter G. O'Sullivan

[57] ABSTRACT

A process for preparing amines comprising contacting an alcohol with a reactant amine in the presence of hydrogen and a catalyst comprising at least one compound containing an element of Group VIB and at least one non-metallic element of Groups IIIA, IVA, and VA of the Periodic Table, the contacting occurring under conditions such that the hydroxyl moiety of the alcohol is replaced by the reactant amine to form an amine product.

21 Claims, No Drawings

AMINATION PROCESS EMPLOYING GROUP VIB METAL CATALYSTS

BACKGROUND OF THE INVENTION

This invention relates to a process for preparing amines from alcohols.

Amines find utility as dispersants, surfactants, chelants, catalysts, curing agents, extenders in polyurethanes, and as starting materials in the preparation of pesticides.

It is well-known that aliphatic amines can be prepared by the reaction of an alkyl halide with ammonia or a reactant amine. The product is an amine hydrohalide salt, which must be neutralized with base in order to recover the valuable amine product. The neutralization produces a waste stream of metal salt, which must be removed. Moreover, the process yields primary, secondary, and tertiary amines, and is therefore not selective.

It is also well-known that aromatic amines can be prepared by the reaction of an aryl halide with ammonia or a reactant amine. This process requires harsh reaction conditions, and selectivity is therefore reduced.

It is known to employ catalysts comprising an oxide of a Group VIB metal in the direct amination of alcohols. For example, U.S. Pat. No. 4,206,150 discloses the reaction of alcohols with ammonia, primary or secondary amines in the presence of a catalyst comprising a mixture of components selected from the groups consisting of copper, copper oxide and mixtures thereof, and molybdenum oxide, tungsten oxide and mixtures thereof.

Japanese Patent No. 48-96475 (1973) discloses the use of tungsten oxide in combination with zirconium oxide or titanium oxide in the amination of hydroxybenzenes by ammonia.

Likewise, U.S. Pat. No. 3,491,148 discloses the amination of mixtures containing n-amyl alcohol and cyclopentanol by ammonia in the presence of a catalyst containing cobalt or nickel, optionally in admixture with a variety of metals including tungsten, preferably, as the oxide.

U.S. Pat. No. 3,714,259 discloses a process for producing linear polyethylenepolyamines comprising reacting an ethyleneamine with an ethanolamine in the presence of a catalyst in the form of oxides of chromium, copper, nickel or cobalt.

The Group VIB metal oxide catalysts identified hereinbefore are prone to sintering during the amination reaction, especially at elevated reaction temperatures. Sintering is a process wherein particles of the catalyst diffuse and agglomerate. Consequently, sintering lowers the surface area of the catalyst and plugs the pores of catalyst supports. Disadvantageously, the catalyst which has sintered usually exhibits a lower catalytic activity.

It would be desirable to have a catalyst which is active and selective in the direct amination of alcohols to amines. It would be more desirable if the catalyst does not sinter at elevated temperatures. Such a catalyst could be operated for prolonged periods of time at elevated temperatures without loss of catalytic activity.

SUMMARY OF THE INVENTION

In one aspect this invention is a process for preparing amines which comprises contacting an alcohol with a reactant amine in the presence of hydrogen and a catalyst. The catalyst comprises at least one compound containing an element of Group VIB and at least one non-metallic element of Groups IIIA, IVA, and VA of the Periodic Table The contacting is conducted under reaction conditions such that the hydroxyl moiety of the alcohol is replaced by the reactant amine to form an amine product.

Advantageously, the Group VIB metal catalysts, identified hereinabove, can be employed in the direct amination of alcohols to amines under moderate process conditions. Moreover, these Group VIB metal catalysts possess high melting points, and are therefore less prone to sintering than the oxide catalysts of the prior art. Accordingly, the catalysts of this invention can be employed in the amination of alcohols for extended reaction periods at elevated temperatures without loss of catalytic activity.

DETAILED DESCRIPTION OF THE INVENTION

The alcohols which are employed in the process of this invention are any which contain at least one hydroxyl moiety bound to a primary or secondary carbon atom. The alcohol can be aliphatic or aromatic. If aliphatic, the alcohol can be linear, cyclic or branched, substituted or unsubstituted, saturated or unsaturated. If substituted, any substituent is acceptable as long as it is inert under the conditions of the amination reaction. The term "inert" means that the substituent does not interfere with or hinder the amination process of this invention. Examples of inert substituents include alkyl moieties, monocyclic aryl moieties and alkylene ether moieties: however, other substituents, not disclosed herein, may be equally inert. Preferably, the substituent is an alkyl moiety containing from 1 to about 12 carbon atoms. If the alcohol is aromatic, it too can be substituted or unsubstituted. If substituted, the substituent should be inert, as defined hereinbefore: and preferably is an alkyl moiety containing from 1 to about 12 carbon atoms. The following list of compounds is exemplary of alcohols which can be employed in the process of this invention however, the list is not meant to be limiting of the scope thereof: methanol, ethanol, 1-propanol, 2-propanol, 1-butanol, 2-butanol, pentanols, hexanols, cyclopentanol, cyclohexanol, phenol, cresol, resorcinol, ethylene glycol, propylene glycol, polyether polyols, monoethanolamine, diethanolamine, triethanolamine, aminoethylethanolamine, and hydroxyethylpiperazine.

Preferably, the alcohol, identified hereinbefore, is an aliphatic alcohol. More preferably, the alcohol is an aliphatic alcohol containing one hydroxyl moiety bound to a primary carbon atom and at least one additional moiety selected from the group consisting of hydroxyl, primary amine and secondary amine functionalities. Most preferably, the alcohol is represented by the general formula:

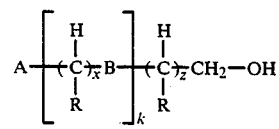

wherein A is OH or NHR: B is NR or O (oxygen); each R is independently hydrogen, a lower alkyl moiety of $C_1$–$C_{12}$ carbon atoms, such as methyl, ethyl or propyl, or a monocyclic aryl moiety, such as phenyl or toluyl: x is an integer from 2 to about 12: k is an integer from 0 to about 150: and z is an integer from 1 to about 12. Preferably, R is hydrogen. More preferably, R is hydrogen, A is NH2, k is 0, and z is 1: and the alcohol is monoethanolamine.

The reactant amines which are employed in the process of this invention include ammonia and any primary or secondary amine. The organic component of these amines can be any aliphatic or aromatic hydrocarbyl moiety. A "hydrocarbyl moiety" contains carbon and hydrogen atoms. The hydrocarbyl moiety may be linear, branched or cyclic. Optionally, the hydrocarbyl moiety can be substituted with an inert substituent, which means that the moiety is unreactive under the conditions of the amination reaction. The following list of compounds is exemplary of amines which can be employed in the process of this invention: however, the list is not meant to be limiting of the scope thereof primary aliphatic amines, such as ethylamine, propylamine, butylamine, pentylamine, hexylamine, and octylamine: secondary aliphatic amines, such as diethylamine, dipropylamine, dihexylamine: alkylenepolyamines, such as ethylenediamine, propylenediamine, diethylenetriamine, and linear and branched triethylenetetramines: alkylene ether polyamines, such as di($\beta$-aminoethyl)ether; and aromatic amines, such as aniline and toluidine.

Preferably, the primary and secondary amines, identified hereinbefore, are represented in the simplest cases by the formula $R_2{}^1NH$, wherein each $R^1$ is independently hydrogen, a $C_1$–$C_{12}$ alkyl moiety monocyclic aromatic moiety. Preferably, the alkylene polyamines and alkylene ether polyamines are represented by the formula:

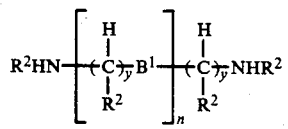

wherein $B^1$ is NR or O: each $R^2$ is independently a hydrogen or a lower alkyl radical of $C_1$–$C_{12}$ carbon atoms, such as methyl, ethyl, propyl, or a monocyclic aromatic radical, such as phenyl or toluyl: each y is independently a positive integer from 1 to about 12, and n is a positive integer from 0 to about 150. Preferably, $B^1$ is NR and $R^2$ is hydrogen. Most preferably, the amine is ethylenediamine or diethylenetriamine.

Any mole ratio of reactants may be used in the process of this invention providing the desired amine products, described hereinafter, are produced. Typically, the alcohol is reacted with at least about one mole equivalent of reactant amine: however, an excess of reactant amine can be advantageously employed. Preferably, the mole ratio of reactant amine to alcohol is in the range from about 0.1:1 to about 20:1. More preferably, the mole ratio of reactant amine to alcohol is in the range from about 1 1 to about 15:1: most preferably from about 2:1 to about 10:1.

Although, preferably, a solvent is not used in the amination reaction, it is within the scope of the invention for a solvent to be optionally used, if desired. Any solvent is acceptable providing it does not react with the alcohol, the reactant amine, and the product amines, and providing the solvent does not decompose under the conditions of the reaction. Some examples of suitable solvents include aromatic hydrocarbons, such as benzene, toluene, and xylene and aliphatic hydrocarbons, such as pentane, hexane, cyclohexane, and octane. The amount of solvent employed depends on the particular reactants and reaction conditions. Any amount of solvent is acceptable that meets the intended purpose of use and does not hinder the reaction. Typically, the solvent will constitute from about 5 weight percent to about 95 weight percent of the feed stream.

It is advantageous, and therefore preferred, to contact the reactants and the catalyst in the presence of hydrogen. Hydrogen serves to accelerate the reaction rate. The hydrogen is introduced into the reaction as gaseous, elemental hydrogen Any amount of hydrogen is employed provided there is sufficient hydrogen present to maintain a practical reaction rate. Preferably, the partial pressure of hydrogen is maintained in a range from about 5 psig to about 3000 psig. More preferably, the partial pressure of hydrogen is maintained in the range from about 50 psig to about 2000 psig: most preferably, from about 100 to about 1000 psig. It is acceptable to dilute the hydrogen with an inert carrier gas, such as nitrogen or helium.

The catalyst of this invention comprises at least one compound containing an element of Group VIB and at least one non-metallic element of Groups IIIA, IVA, and VA of the Periodic Table. The Group VIB elements include chromium (Cr), molybdenum (Mo), and tungsten (W). Preferably, the Group VIB element is tungsten. The non-metals of Groups IIIA, IVA and VA include boron (B), carbon (C), silicon (Si), nitrogen (N), phosphorus (P), and arsenic (As). Preferably, the non-metal is selected from the group consisting of B, C, N, Si, and P. More preferably, the non-metal is selected from the group consisting of B, C, and N. Most preferably, the catalyst is a tungsten boride, tungsten carbide or tungsten nitride. The following list of binary compounds is exemplary of the compounds which are suitable for the process of this invention: however, the list is only a partial recitation of all of the suitable catalysts, and as such is not meant to be limiting of the scope of the process: CrB, $Cr_2B$, $Cr_3C_2$, $Cr_3Si$, CrN, $Cr_2N$, CrP, $CrP_2$, $Cr_2As$, CrAs, $Mo_2B$, $Mo_3B_2$, $Mo_2C$, MoC, $Mo_5Si_3$, $Mo_3N$, $Mo_2N$, MoN, WB, $W_2B$, $W_2B_5$, $WB_4$, WC, $W_2C$, $WSi_2$, $W_3Si$, WN, $W_2N$, $WN_2$, WP, $WP_2$, and mixtures of the above. Compositions containing non-stoichiometric proportions of the Group VIB element and the Groups IIIA, IVA, and VA non-metal are also suitable catalysts for the process of this invention. Preferably, the non-stoichiometric compositions have the formula $MX_x$ wherein M is the Group VIB element, X is any of the non-metals identified hereinbefore, and x is a positive number ranging from about 0.5 to about 2.0. It is further within the scope of this invention for the catalyst to comprise a ternary compound of the Group VIB element with any two of the non-metals identified hereinbefore, such as tungsten carbonitride. In addition, ternary compounds containing the Group VIB element, one of the aforementioned non-metals, and oxygen, such as tungsten oxyborides, tungsten oxycarbides, and tungsten oxynitrides, fall within the scope of the invention. Preferably, however, the oxygen content of these ternary compounds is less than about 50 mole percent of the total moles of non-metals: more preferably, less than about 30 mole percent of the total moles of non-metals. Most preferably, the catalyst contains less than about 10 mole percent of the total moles of non-metals as oxygen.

The catalysts, described hereinbefore, can be obtained commercially, or prepared. The common preparations are referenced in *Comprehensive Inorganic Chemistry*, Volume 3, edited by J. C. Bailar, Jr., H. J. Emeléus, Sir R. Nyholm, and A. F. Trotman-Dickenson, Pergamon Press 1973, pp. 623-769. Tungsten borides and carbides are available commercially from Alfa and Kennemetal Companies. Tungsten nitrides can be purchased from the Aesar and Alfa Companies: or alternatively can be prepared as described hereinafter.

Optionally, the catalysts, which are employed in the process of this invention, can be applied to a support material. The support material functions to increase the surface area of the catalyst, thereby promoting higher catalytic activity. Any support material which does not hinder the amination reaction is acceptable. Suitable supports include the refractory oxides, such as alumina, zirconia, boria, thoria, magnesia, titania, tantala, silica, kielselguhr, and mixtures of these materials. The support material typically has a surface area of at least about $0.1 \, m^2/g$. Preferably, the support material has a surface area from about $5 \, m^2/g$ to about $600 \, m^2/g$: more preferably from about $50 \, m^2/g$ to about $200 \, m^2/g$. These surface areas are measured by the Brunauer-Emmett-Teller (BET) method. The BET method is described by R. B. Anderson in Experimental Methods in Catalytic Research, Academic Press, 1968, pp. 48-66. The catalyst can be applied to the support material in any known fashion, such as by the impregnation technique or by precipitation in situ from the catalyst preparation reaction.

The preferred catalyst for the process of this invention comprises tungsten nitride and a support material. This composition can be prepared in any suitable manner. Preferably, however, the composition is prepared by applying an oxide of tungsten to a support material, and contacting the supported tungsten oxide with ammonia under conditions sufficient to produce a supported tungsten nitride catalyst. A detailed description of the catalyst preparation is given hereinbelow.

A mixture is prepared containing a support material and an aqueous solution of hydrogen peroxide and a tungsten salt. The tungsten salt is any one which has a water solubility of at least about $1.0 \, g/l$. Examples of water-soluble tungsten salts include $(NH_4)_2WO_4$ and para-ammonium tungstate. Preferably, the water-soluble salt is a tungsten oxide: more preferably, $(NH_4)_2WO_4$. In preparing the aqueous solution, any amount of water may be used providing all of the tungsten salt is dissolved to make a homogeneous solution. Preferably, the tungsten salt is added to water to form a solution that ranges from about 1 weight percent to about 30 weight percent tungsten salt. In addition to the dissolved salt, the solution also contains hydrogen peroxide. The hydrogen peroxide aids in solubilizing the tungsten salt. Any amount of hydrogen peroxide which is capable of completing the solubilization is acceptable. Preferably, the minimum amount of hydrogen peroxide which solubilizes the tungsten salt is employed. Preferably, the desired amount of hydrogen peroxide is obtained by adding the appropriate volume of a 30 weight percent aqueous hydrogen peroxide solution. It is not critical when or how the hydrogen peroxide is added to the water. For example, the hydrogen peroxide may be added to the water before the addition of the tungsten salt, or after. Preferably, the hydrogen peroxide is added before the addition of the tungsten salt.

After the aqueous solution is prepared, it is added with stirring to a support material. The support material is any refractory oxide, such as alumina, silica, aluminum-silicates, titania, or any of the supports disclosed hereinbefore. Preferably, the support material is alumina or titania. The amount of support material is any which will provide a homogenous distribution of the tungsten oxide over the surface of the support. Preferably, enough support material is employed to give a dried mixture which is not greater than about 70 weight percent tungsten oxide. More preferably, enough support material is employed to give a dried mixture which is not greater than about 30 weight percent tungsten oxide. The mixture containing the aqueous tungsten oxide solution and the support material is dried to yield a dried mixture comprising a supported tungsten oxide. In addition to removing water, the drying serves to remove ammonia, to decompose residual peroxide, and to set the tungsten oxide on the surface of the support material. Any drying technique well-known in the art, such as rotary evaporation, is acceptable. Optionally, the dried mixture can be further dried in air for several hours.

In the final preparative step, the supported tungsten oxide, described hereinbefore, is nitrided by contacting the mixture with ammonia under conditions sufficient to form the supported tungsten nitride catalyst. The nitridification is conducted in any suitable pressure reactor or continuous flow reactor. Generally, the nitridification comprises heating the supported tungsten oxide in a stream of ammonia for a time sufficient to reduce the tungsten oxide to a supported tungsten nitride catalyst. The quantity of ammonia needed for the nitridification will vary depending on the quantity of catalyst to be reduced. It is only important that the catalyst be exposed to a sufficient quantity of ammonia to ensure complete reduction of the tungsten oxide. A "sufficient" quantity of ammonia is defined as a mole ratio of ammonia to tungsten oxide of at least about 1 1. Preferably, the mole ratio of ammonia to tungsten oxide is at least about 5:1: more preferably, at least about 10 1. Any temperature and heating time are acceptable, providing they promote the nitridification without adverse results, such as reduction to tungsten metal. Preferably, the temperature of the nitridification is in the range from about 500° C. to about 750° C. More preferably, the nitridification temperature is in the range from about 550° C. to about 650° C., so as to avoid the formation of tungsten metal. Preferably, the heating time is in the range of from about 10 minutes to about 10 hours: more preferably, from about 1 hour to about 5 hours. Typically, the reaction is finished in less than 1 hour: however, it is not deleterious to heat for a longer time to ensure complete reaction.

The supported tungsten nitride catalyst prepared as described hereinbefore can be analyzed by X-ray diffraction analysis. The predominant molecular species on the surface of the support is found to be $W_2N$.

The amount of catalyst, which is employed in the process of this invention, varies over a wide range depending on the alcohol and amine reactants and on the particular reaction conditions employed. Any amount of catalyst which is effective in promoting the amination reaction is acceptable. Typically for a batch reactor, the amount of catalyst employed is in the range from about 0.1 weight percent to about 30 weight percent based on the weight of reactant amine. Preferably, the amount of catalyst employed is in the range from about 1 weight percent to about 20 weight percent based on the weight of reactant amine.

The process of this invention can be conducted in any suitable reactor, including batch and continuous flow reactors. By way of illustration of a batch process, a high pressure stirred autoclave is charged with alcohol, reactant amine, and catalyst, pressurized with hydrogen, and heated to the reaction temperature. After the reaction is allowed to proceed for the desired length of time, the autoclave is cooled, the excess hydrogen vented, and the products worked up by conventional methods, such as gas phase chromatography. By way of illustration of a continuous flow process, a vertical, high pressure column is charged with catalyst, and the alcohol and reactant amine are supplied at the top of the column. At the same time hydrogen is metered into the column in a cocurrent or countercurrent flow. The appropriate temperature and pressure are maintained throughout. The reaction product is removed from the bottom of the column, separated from hydrogen, and analyzed by conventional methods, such as gas phase chromatography.

The alcohol and reactant amine are contacted with the catalyst at any operable temperature which produces the desired amine product. Typically, the temperature is in the range from about 200° C. to about 400° C. Preferably, the temperature is in the range from about 225° C. to about 350° C. More preferably, the temperature is in the range from about 260° C. to about 315° C. Below the preferred lower limit the conversion of alcohol may be low. Above the preferred upper limit selectivity to the desired amine product may decrease.

Likewise, the reactants are contacted with the catalyst at any operable pressure which produces the desired amine product. Typically, the pressure is sufficient to maintain the alcohol and amine reactants in the liquid state at the temperature of the reaction. Preferably, the pressure is in the range from about atmospheric to about 4000 psig. More preferably, the pressure is in the range from about 100 psig to about 3000 psig. Most preferably, the pressure is in the range from about 400 psig to about 2000 psig. In batch reactors the pressure is autogenous, and will depend on the boiling points of the reactants, the temperature of the reaction, and the amount of hydrogen.

When the process of this invention is conducted in a continuous flow reactor, the flow rate of the reactants can be varied. Generally, the alcohol and the amine reactants are premixed to form a feed stream, which is flowed into the reactor at any operable flow rate which allows for reaction to amine products. The flow rate is best expressed as the liquid hourly space velocity and is given in units of grams of total reactants per milliliter of total reactor volume per hour, g ml$^{-1}$ hr$^{-1}$. It is preferred to employ a liquid hourly space velocity in the range from about 0.1 g ml$^{-1}$ hr$^{-1}$ to about 10.0 g ml$^{-1}$ hr$^{-1}$ more preferably in the range from about 0.5 g ml$^{-1}$ hr$^{-1}$ to about 4.0 g ml$^{-1}$ hr$^{-1}$. It is understood that the liquid hourly space velocity controls the residence time of the reactants in a continuous flow reactor.

When the process of this invention is conducted in a batch reactor, the reaction time determines the length of contact between the reactants and the catalyst. Any reaction time is acceptable which allows the amination reaction to proceed to the desired degree of conversion. The reaction time depends on the quantity of reactants, the quantity of catalyst, the temperature of the reaction and the desired degree of conversion. Preferably, the reaction time in a batch reactor is in the range from about 1 hour to about 20 hours.

The products, which are produced in the process of this invention, are amines formed by the displacement of the hydroxyl moiety of the alcohol by the reactant amine. For example, if the alcohol is n-pentanol and the reactant amine is n-butylamine, the product is n-pentyl-n-butylamine. If the alcohol is phenol and the reactant amine is isopropylamine, the product is N-phenyl-N-isopropylamine. If the alcohol is a diol, one or both of the hydroxyl moieties can be displaced by the reactant amine. In the special case involving the amination of an alkanolamine by an alkyleneamine, two competing reactions can occur. In one reaction the alkanolamine is aminated by the reactant alkyleneamine. In the competing reaction the alkanolamine is aminated by the amine moiety of the alkanolamine. Operating simultaneously, the reactions give rise to a product mixture containing polyalkylenepolyamine oligomers. Particularly preferred products are the polyalkylenepolyamines which are represented by the general formula:

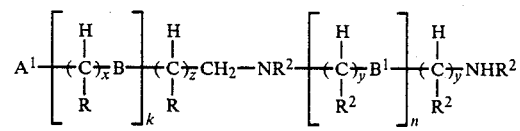

wherein B, B$^1$, R, R$^2$, x, y, z, k, and n are defined L hereinbefore; and wherein A$^1$ is OH, NR or:

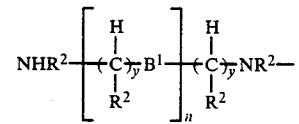

Preferably, R and R$^2$ are hydrogen. More preferably, R and R$^2$ are hydrogen, and k and n are 0. Most preferably, the polyalkylenepolyamine products are diethylenetriamine, triethylenetetramine, and tetraethylenepentamine The conversion of alcohol and the selectivities to amine products vary in the process of this invention depending on the reactants, the form of the catalyst, and the process conditions. For the purposes of this invention "Conversion" is defined as the weight percentage of alcohol lost from the feed stream as a result of reaction. Typically, the conversion is at least about 3 weight percent. Preferably, the conversion is at least about 14 weight percent: more preferably at least about 30 weight percent: most preferably, at least about 50 weight percent. Likewise, for the purposes of this invention "Selectivity" is defined as the weight percentage of converted alcohol which forms a particular amine product.

In the specific case of the amination of an alkanolamine by an alkyleneamine, the invention yields polyalkylenepolyamines enriched in non-cyclic compounds. "Non-cyclic" compounds are defined as linear and branched compounds which do not possess a nitrogen-containing heterocycle. Examples of non-cyclic products include diethylenetriamine, linear and branched triethylenetetramines, and linear and branched tetraethylenepentamines. Lesser amounts of cyclic materials, which do possess a nitrogen-containing heterocycle, are also produced. Examples of cyclic products include piperazine and N-aminoethylpiperazine. Typically, the selectivity for non-cyclic polyalkylenepolyamines is at least about 15 weight percent. Preferably, the selectivity for non-cyclic polyalkylenepolyamines is at least about 30 weight percent: more preferably, about 60 weight percent.

In those reactions where it is applicable, the efficiency of forming non-cyclic compounds can be measured by calculating the weight ratio of diethylenetri-

EXAMPLE 1

The amination of monoethanolamine by diethylenetriamine is conducted according to the General Procedure, described hereinbefore. The catalyst is an unsupported tungsten carbide, WC (Alfa). The process conditions and results are presented in Table I.

TABLE I

| Exp. | Catalyst | Amt Cata. (g) | Time (hr) | Temp (°C.) | % MEA Conversion | % Selectivity (DETA-MEA free basis) | | | | | | % NC TETA [1] |
|---|---|---|---|---|---|---|---|---|---|---|---|---|
| | | | | | | EDA | TETA | TEPA | PIP | AEP | AEEA | |
| 1 | WC | 1.0 | 5.0 | 310 | 16 | 35 | 26 | 25 | 2 | 2 | 9 | 90.5 |
| 2 | WC/WC$_2$ | 1.0 | 5.0 | 330 | 33 | 37 | 22 | 28 | 3 | 2 | 8 | 75.7 |
| 3(a) | WB/WB$_2$ | 1.0 | 5.0 | 310 | 14 | 25 | 35 | 29 | 3 | 1 | 6 | 87.0 |
| 3(b) | WB/WB$_2$ | 6.3 | 5.0 | 315 | 36 | 19 | 27 | 36 | 7 | 9 | 1 | 81.7 |
| 4(a) | WN/WN$_2$ | 6.0 | 8.0 | 310 | 89 | 16 | 25 | 33 | 3 | 23 | 0 | 0.1 |
| 4(b) | WN/WN$_2$ | 4.5 | 8.0 | 290 | 95 | 14 | 27 | 35 | 10 | 13 | 1 | 66.3 |

[1] % NC TETA = weight percentage of triethylenetetramines which are non-cyclic.

amine to piperazine, abbreviated DETA/PIP. Preferably, the DETA/PIP weight ratio is at least about 1. More preferably, the DETA/PIP weight ratio is at least about 2: most preferably, at least about 3. Another measure of the efficiency of forming non-cyclic products is given by the weight percentage of triethylenetetramines which are non-cyclic, %NC TETA. Preferably, the %NC TETA is at least about 45 weight percent. More preferably, the %NC TETA is at least about 65 weight percent: most preferably, at least about 85 weight percent.

The following examples illustrate the invention, but are not intended to be limiting of the scope thereof. All percentages are weight percent, unless noted otherwise. In some instances the following abbreviations are used to indicate the reactants and products:

MEA—monoethanolamine
EDA—ethylenediamine
AEEA—N-(2-aminoethyl)ethanolamine
DETA—diethylenetriamine
TETA—triethylenetetramine
TEPA—tetraethylenepentamine
PIP—piperazine
AEP—N-(2-aminoethyl)piperazine

General Procedure

An Autoclave Engineers stirred batch reactor (300 ml capacity), fitted with a pressure gauge and a thermocouple to monitor temperature, is loaded with a quantity of solid catalyst and 50 ml of a solution comprising monoethanolamine and the reactant amine. The reactant amine/MEA mole ratio is 2:1. The reactor is sealed, flushed with nitrogen, and pressurized with hydrogen to about 365 psig. The reactor is heated to the desired reaction temperature, and held at that temperature for the desired reaction time. The reactor is then cooled to room temperature, and the contents are analyzed by gas phase chromatography. A CAM (Carbowax amine deactivated) capillary column (15 m×0.25 mm dia.) is employed for the total analysis of amine products. Isomer distributions are determined on an SE-54 capillary column (30 m×0.25 mm dia.).

It is seen that WC catalyzes the amination of monoethanolamine to a mixture of polyethylenepolyamines enriched in non-cyclic compounds. This result is reflected in the low quantity of cyclic products (PIP and AEP) and in the high %NC TETA obtained.

EXAMPLE 2

The amination of monoethanolamine by diethylenetriamine is conducted according to the General Procedure, described hereinbefore, with a catalyst of unsupported WC/WC$_2$ (Kennemetal). The process conditions and results are presented in Table I. It is seen that WC/WC$_2$ catalyzes the amination of monoethanolamine to a mixture of polyethylenepolyamines enriched in non-cyclic compounds.

EXAMPLE 3 (a-b)

The amination of monoethanolamine by diethylenetriamine is conducted according to the General Procedure, described hereinbefore, with a catalyst of unsupported WB/WB$_2$ (Alfa). The process conditions and results are presented in Table I. It is seen that WB/WB$_2$ catalyzes the amination of monoethanolamine to polyethylenepolyamines enriched in non-cyclic compounds.

EXAMPLE 4 (a-b)

The amination of monoethanolamine by diethylenetriamine is conducted according to the General Procedure, described hereinbefore, with a catalyst of unsupported WN/WN$_2$ (Alfa). The process conditions and results are presented in Table I. It is seen from the high conversion of MEA that WN/WN$_2$ is a highly active catalyst. At a reaction temperature of 290° C. (4b) the products are predominately non-cyclic compounds. However, at a reaction temperature of 310° C. (4a) the products are predominately cyclic materials.

EXAMPLE 5

The amination of monoethanolamine by ethylenediamine is conducted according to the General Procedure, described hereinbefore. The catalyst is unsupported tungsten carbide (Aesar). The process conditions and results are presented in Table II.

TABLE II

| Exp. | Catalyst | Amt Cata. (g) | Time (hr) | Temp (°C.) | % MEA Conversion | % Selectivity (EDA-MEA free basis) | | | | | | % NC TETA [1] |
|---|---|---|---|---|---|---|---|---|---|---|---|---|
| | | | | | | DETA | TETA | TEPA | PIP | AEP | AEEA | |
| 5 | WC | 10.0 | 42.0 | 255 | 23 | 6 | 3 | 0 | 71 | 4 | 16 | NA [2] |

TABLE II-continued

| Exp. | Catalyst | Amt Cata. (g) | Time (hr) | Temp (°C.) | % MEA Conversion | % Selectivity (EDA-MEA free basis) | | | | | | % NC TETA [1] |
|---|---|---|---|---|---|---|---|---|---|---|---|---|
| | | | | | | DETA | TETA | TEPA | PIP | AEP | AEEA | |
| 6 | WB/WB$_2$ | 2.0 | 5.0 | 315 | 7 | 65 | 2 | 0 | 18 | 14 | 0 | NA [2] |
| 7(a) | WN/WN$_2$ | 6.0 | 12.0 | 260 | 14 | 67 | 4 | 2 | 2 | 5 | 20 | 87 |
| 7(b) | WN/WN$_2$ | 6.0 | 30.0 | 260 | 68 | 34 | 23 | 14 | 13 | 12 | 2 | 57 |
| 7(c) | WN/WN$_2$ | 6.0 | 37.0 | 260 | 77 | 26 | 24 | 21 | 14 | 14 | 1 | 47 |

[1] % NC TETA = percentage of triethylenetetramines which are non-cyclic.
[2] NA = not available; TETA fraction too small.

The DETA/PIP ratio is calculated to be 0.08. It is seen that WC catalyzes the amination of monoethanolamine to predominately cyclic products, including piperazine and aminoethylpiperazine.

EXAMPLE 6

The amination of monoethanolamine by ethylenediamine is conducted according to the General Procedure, described hereinbefore. The catalyst is unsupported WB/WB$_2$ (Alfa). The process conditions and results are presented in Table II. The DETA/PIP ratio is calculated to be 3.6. It is seen that WB/WB$_2$ catalyzes the amination of monoethanolamine to predominately non-cyclic polyethylenepolyamines.

EXAMPLE 7(a-c)

The amination of monoethanolamine by ethylenediamine is conducted according to the General Procedure, described hereinbefore. The catalyst is unsupported WN/WN$_2$ (Alfa). The process conditions and results are presented in Table II. The DETA/PIP ratios are calculated to be (7a) 33.5, (7b) 2.6, and (7c) 1.9. Moreover, it is seen that at conversions less than 70 percent (7a-b), the majority of the TETA fraction consists of non-cyclic homologues. Thus, WN/WN2 catalyzes the amination of monoethanolamine to polyethylenepolyamines enriched in non-cyclic products.

COMPARATIVE EXPERIMENT 1

The amination of monoethanolamine by ethylenediamine is carried out as in Example 5, except that unsupported tungsten metal (10.0 g: Cerac) is employed as the catalyst. The reaction is run for 48 hours at 290° C. with the following results: MEA conversion, 48 percent: selectivities (EDA-MEA free basis) to DETA, 6 percent: TETA, 4 percent: PIP, 90 percent; and only traces of TEPA, AEP and AEEA. When Comparative Experiment 1 is compared with Examples 7(a-c), it is seen that the unsupported tungsten nitride catalyst is more active than tungsten metal. Moreover, the tungsten nitride catalyst produces significantly fewer cyclic products than does tungsten metal.

EXAMPLES 8(a-b)

(NH$_4$)$_2$WO$_4$ (15.0 g: 52.8 mmoles) is added to about 400 ml of water to which 25 ml of ammonium hydroxide and 5 ml of 30 percent hydrogen peroxide are added. The ammonium tungstate is dissolved slowly by heating the mixture to about 80° C. with stirring. After a clear homogenous solution forms, the solution is cooled to room temperature. The solution is added to a flask containing 25.0 g of alumina (Catapal SB 20-35 mesh: 280 m$^2$/g). The resulting mixture is rotary evaporated to remove water, and then calcined in a muffle furnace at 300° C. overnight to yield a supported ammonium tungstate or tungsten oxide.

The nitridification/reduction of the supported ammonium tungstate or tungsten oxide is conducted in a stainless steel, downflow reactor. The temperature of the supported ammonium tungstate or tungsten oxide is raised from 22° C. to 500° C. in 60 minutes under a flow of nitrogen at a flow rate of 20 cc/minute. At 500° C. ammonia is added to the nitrogen stream at a rate of 15 cc/minute. The supported tungstate is held at 500° C. under the nitrogen-ammonia stream for one hour. The temperature is raised to (a) 624° C. or (b) 750° C. over 60 minutes, and then held for 16 hours. The temperature is thereafter lowered to 300° C. over 60 minutes, at which time the flow of ammonia is stopped. The heater is turned off and the reactor is cooled to room temperature to yield the supported tungsten nitride catalysts. Analysis of the catalysts by X-ray diffraction indicates WN$_2$ is present on the surface of catalyst 8(a), and a mixture of predominately W$_2$N and some W metal is present on the surface of catalyst 8(b).

Catalysts 8(a) and 8(b) are tested in the amination of monoethanolamine by ethylenediamine, as described in the General Procedure, with the results found in Table III.

TABLE III

| Exp. | Amt Cata. (g) | Time (hr) | Temp (°C.) | % MEA Conversion | % Selectivity (EDA-MEA free basis) | | | | | | % NC TETA [1] |
|---|---|---|---|---|---|---|---|---|---|---|---|
| | | | | | DETA | TETA | TEPA | PIP | AEP | AEEA | |
| 8(a) | 3.0 | 8.0 | 310 | 66 | 36 | 23 | 12 | 11 | 6 | 14 | 77.8 |
| 8(b) | 2.0 | 8.0 | 310 | 33 | 36 | 6 | 4 | 16 | 3 | 35 | 95.0 |
| 9 | 2.0 | 8.0 | 310 | 49 | 45 | 12 | 4 | 20 | 1 | 18 | 50.0 |

[1] % NC TETA = percentage of triethylenetetramines which are non-cyclic.

The DETA/PIP ratios are calculated to be (8a) 3.3 and (8b) 2.3. It is seen that tungsten nitride supported on alumina is a good catalyst for the amination of monoethanolamine to a mixture of polyethylenepolyamines enriched in non-cyclic compounds.

EXAMPLE 9

Para-ammonium tungstate (15.0 g: Amends Chemical Company) is added to about 400 ml of water containing 5 ml of 30 weight percent hydrogen peroxide. The ammonium tungstate is dissolved by heating at 80° C. for 3 hours. The solution is cooled to room temperature, and added to a flask containing titania (25.0 g: Saki CS 200, 20-35 mesh). Water is removed from the mixture by rotary evaporation to obtain a solid. The solid is dried in a muffle furnace at 300° C. over the weekend.

The nitridification of the dried solid is carried out as in Example 8(a) to yield a tungsten nitride catalyst supported on titania. The X-ray diffraction pattern of the supported tungsten nitride catalyst shows an amorphous material.

The tungsten nitride catalyst supported on titania is used in the amination of monoethanolamine by ethylenediamine according to the General Procedure, described hereinbefore, with the results given in Table III. The DETA/PIP ratio is 2.3. It is seen that tungsten nitride supported on titania is a good catalyst for the amination of monoethanolamine to polyethylenepolyamines enriched in non-cyclic compounds.

What is claimed is:

1. A process for preparing an amine comprising contacting an alcohol with a reactant amine in the presence of hydrogen and a catalyst selected from the group consisting of:
    (1) Binary compounds consisting essentially of an element of Group VIB and a non-metallic element selected form Groups IIIA, IVA, or VA;
    (2) Ternary compounds consisting essentially of an element of Group VIB and two non-metallic elements selected from Groups IIIA, IVA, and VA; and
    (3) Ternary compounds consisting essentially of an element of Group VIB, oxygen, and one non-metallic element selected from Groups IIIA, IVA, or VA, such that the oxygen content of the compound is less than about 10 mole percent of the total moles of non-metals,
the contacting occurring under conditions such that a hydroxyl moiety of the alcohol is replaced by the reactant amine to form an amine product.

2. The process of claim 1 wherein the alcohol is aliphatic.

3. The process of claim 2 wherein the alcohol is represented by the formula:

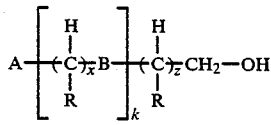

wherein A is OH or NHR: B is NR or O: each R is independently hydrogen, a lower alkyl moiety of $C_1$–$C_{12}$ carbon atoms, or a monocyclic aryl moiety: x is an integer from 2 to about 12: k is an integer from 0 to about and z is an integer from 1 to about 12.

4. The process of claim 3 wherein the alcohol is monoethanolamine.

5. The process of claim 1 wherein the reactant amine is an aliphatic amine.

6. The process of claim 5 wherein the reactant amine is represented by the formula:

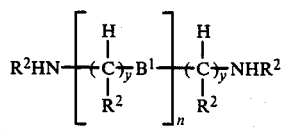

wherein $B^1$ is O or $NR^2$; each $R^2$ is independently a hydrogen or a lower alkyl moiety of $C_1$–$C_{12}$ carbon atoms, or a monocyclic aryl moiety; each y is independently a positive integer from 1 to about 12, and n is a positive integer from 0 to about 150.

7. The process of claim 6 wherein the reactant amine is ethylenediamine.

8. The process of claim 6 wherein the reactant amine is diethylenetriamine.

9. The process of claim 1 wherein the Group VIB element is tungsten.

10. The process of claim 1 wherein the non-metallic element is selected from the group consisting of boron, carbon, nitrogen, silicon, phosphorus, and mixtures thereof.

11. The process of claim 10 wherein the non-metallic element is selected from the group consisting of boron, carbon, and nitrogen.

12. The process of claim 1 wherein the catalyst is tungsten boride.

13. The process of claim 1 wherein the catalyst is tungsten carbide.

14. The process of claim 1 wherein the catalyst is tungsten nitride.

15. The process of claim 1 wherein the catalyst is supported on a refractory oxide.

16. The process of claim 1 wherein the temperature is in the range from about 200° C. to about 400° C.

17. The process of claim 1 wherein the hydrogen partial pressure is in the range from about atmospheric to about 4000 psig.

18. The process of claim 1 wherein the amine product is represented by the general formula:

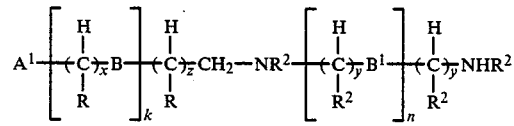

wherein B and $B^1$ are each independently NR or O; each R and $R^2$ is independently hydrogen, a lower alkyl moiety of $C_1$–$C_{12}$ carbon atoms, or a monocyclic aryl moiety; x is an integer from 2 to about 12; each y and z are independently a positive integer from 2 to about 12; k and n are each independently positive integers from 0 to about 150; and wherein A1 is OH, NR or:

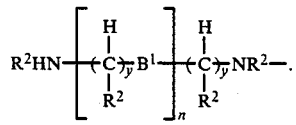

19. The process of claim 18 wherein the selectivity for non-cyclic polyalkylenepolyamines is at least about 30 weight percent.

20. A process for preparing predominately non-cyclic polyethylenepolyamines comprising contacting monoethanolamine with an ethylenediamine in the presence of hydrogen and a catalyst consisting essentially of tungsten boride or tungsten nitride, the contacting occurring under reaction conditions such that a mixture of polyethylenepolyamines is formed, wherein the diethylenetriamine/piperazine weight ratio is at least about 2, and the percentage of non-cyclic triethylenetetramines is at least about 45 weight percent.

21. The process of claim 18 wherein the selectivity for non-cyclic polyalkylenepolyamines is at least about 60 weight percent.

* * * * *